(12) United States Patent
Bae et al.

(10) Patent No.: US 8,043,212 B1
(45) Date of Patent: Oct. 25, 2011

(54) METHODS FOR TREATING CERVICAL VERTEBRAE THROUGH AN ACCESS DEVICE

(75) Inventors: Hyun W. Bae, Santa Monica, CA (US); Robert F. Heary, Summit, NJ (US); Alan S. Hilibrand, Merion Station, PA (US); Ashwini D. Sharan, Mount Laurel, NJ (US); Jeffrey C. Wang, Sherman Oaks, CA (US); Gene P. DiPoto, Upton, MA (US); John D. Unger, Wrentham, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1669 days.

(21) Appl. No.: 11/238,109

(22) Filed: Sep. 27, 2005

Related U.S. Application Data

(60) Provisional application No. 60/625,782, filed on Nov. 5, 2004.

(51) Int. Cl.
*A61B 1/32* (2006.01)

(52) U.S. Cl. .................. 600/215; 600/222; 600/225

(58) Field of Classification Search .......... 600/201–234; 141/333–334, 337; 604/103, 103.07, 103.14, 604/104, 106–107, 528, 96.01, 97.01, 509; 220/254.9, 254.1–254.3, 212, 810–812, 826, 220/192, 203, 628, 634, 638, 720; 403/61, 403/82; 285/184, 224, 145.2; 606/86 R, 606/279, 99
See application file for complete search history.

(56) References Cited

U.S. PATENT DOCUMENTS

| | | | | |
|---|---|---|---|---|
| 2,605,582 A | * | 8/1952 | Allen | 43/100 |
| 5,004,353 A | * | 4/1991 | Martin | 366/349 |
| 5,107,824 A | * | 4/1992 | Rogers et al. | 602/16 |
| 5,121,779 A | * | 6/1992 | Green | 141/337 |
| 5,542,774 A | * | 8/1996 | Hoy | 403/116 |
| 6,139,493 A | * | 10/2000 | Koros et al. | 600/215 |
| 6,524,320 B2 | * | 2/2003 | DiPoto | 606/108 |
| 7,029,124 B2 | | 4/2006 | Dubin et al. | |
| 7,144,396 B2 | | 12/2006 | Shluzas | |
| 7,226,451 B2 | * | 6/2007 | Shluzas et al. | 606/86 R |
| 2003/0073998 A1 | * | 4/2003 | Pagliuca et al. | 606/61 |
| 2003/0083688 A1 | * | 5/2003 | Simonson | 606/191 |
| 2003/0153927 A1 | * | 8/2003 | DiPoto et al. | 606/108 |
| 2003/0191371 A1 | * | 10/2003 | Smith et al. | 600/210 |
| 2003/0195493 A1 | * | 10/2003 | Davison et al. | 606/1 |
| 2003/0199885 A1 | * | 10/2003 | Davison et al. | 606/108 |
| 2004/0230100 A1 | | 11/2004 | Shluzas | |
| 2005/0070765 A1 | * | 3/2005 | Abdelgany et al. | 600/214 |

(Continued)

FOREIGN PATENT DOCUMENTS

WO 2006045089 4/2006

(Continued)

*Primary Examiner* — Eduardo C Robert
*Assistant Examiner* — Steven Cotroneo
(74) *Attorney, Agent, or Firm* — Seager Tufte Wickhem LLC

(57) ABSTRACT

A method for providing treatment at or near a cervical region of the spine of a patient is provided. An incision is formed in the skin of a patient above the cervical region. An elongate body is inserted into the patient through the incision, the elongate body having a distal portion, a proximal portion, an outer surface, and an inner surface, the inner surface defining a passage extending through the elongate body. The elongate body is advanced until a distal end thereof resides at or near the cervical region of the spine. The size of the passage in the distal portion is increased relative to the size of the proximal portion.

1 Claim, 24 Drawing Sheets

U.S. PATENT DOCUMENTS

| | | |
|---|---|---|
| 2005/0075644 A1 | 4/2005 | DiPoto et al. |
| 2005/0090822 A1 | 4/2005 | DiPoto |
| 2005/0090899 A1 | 4/2005 | DiPoto |
| 2005/0216002 A1* | 9/2005 | Simonson ............ 606/61 |
| 2005/0245942 A1 | 11/2005 | DiPoto |
| 2006/0052812 A1 | 3/2006 | Winer |
| 2006/0195017 A1 | 8/2006 | Shluzas et al. |
| 2007/0021750 A1 | 1/2007 | Shluzas et al. |

FOREIGN PATENT DOCUMENTS

| | | |
|---|---|---|
| WO | 2006058079 | 6/2006 |

\* cited by examiner

METHODS FOR TREATING CERVICAL VERTEBRAE THROUGH AN ACCESS DEVICE

CROSS-REFERENCE TO RELATED APPLICATIONS

This application claims the benefit of U.S. Provisional Application No. 60/625,782, filed Nov. 5, 2004, which is hereby expressly incorporated by reference herein in its entirety.

BACKGROUND OF THE INVENTION

1. Field of the Invention

This application is directed to apparatuses and methods of providing access to a region of the spine. More particularly, this application is directed to apparatuses and methods that can provide access to upper spinal regions, such as the cervical and thoracic regions, and other similar spinal regions and to procedures that are more easily performed at an angle to the midline of the spine.

2. Description of the Related Art

Spinal surgery presents significant difficulties to the physician attempting to reduce chronic back pain or correct spinal deformities without introducing additional trauma due to the surgical procedure itself. In order to access the vertebrae to perform spinal procedures, the physician is typically required to make large incisions and cut or strip muscle tissue surrounding the spine. In addition, care must be taken not to injure nerve tissue in the area. Consequently, traditional surgical procedures of this type carry high risks of scarring, pain, significant blood loss, and extended recovery times.

Apparatuses for performing minimally invasive techniques have been proposed to reduce the trauma of posterior spinal surgery by reducing the size of the incision and the degree of muscle stripping in order to access the vertebrae. One such apparatus provides a constant diameter cannula that is made narrow in order to provide a small entry profile. As a result, the cannula provides minimal space for the physician to observe the body structures and manipulate surgical instruments in order to perform the required procedures. Many spinal conditions arise in the thoracic and lumbar region of the spine, where spinal anatomy can be approached along a vertical plane parallel to a vertical plane through the spinal mid-line. However, some spinal ailments arise in spinal regions where the approach to the spine is generally at an angle to the midline, e.g., in the cervical region. Also, some lumbar and thoracic procedures are performed generally at an angle to the midline.

SUMMARY OF THE INVENTION

There is a need in the art for systems and methods for treating the spine that provide minimally invasive access to the spine such that a variety of procedures, e.g., cervical procedures and other procedures performed generally at an angle to the midline, and preferably the entire procedure or at least a substantial portion thereof, can be performed via a single access device.

In one embodiment, a device provides access to a spinal location within a patient. The device comprises an elongate body having a proximal portion, a distal portion, an outer surface, and an inner surface. The inner surface defines a passage extending through the elongate body along a longitudinal axis. The passage enables surgical instruments to be inserted therethrough. The distal portion is configured to conform to spinal anatomy, e.g., anatomy of a cervical or a thoracic spinal location.

Several variations of the embodiment described above are provided below to describe other features that may be present in certain embodiments. In variations of the embodiment, one or more of the following features are included in a device that provides access to a spinal location within a patient. In one variation of the embodiment described above, the distal portion further comprises a first skirt portion and a second skirt portion. The first skirt portion extends a first length from a proximal end of the elongate body. The second skirt portion has a configuration when inserted into, e.g., positioned within, the patient wherein the second skirt portion extends a second length from the proximal end. The second length is greater than the first length.

In another variation, the second skirt portion is configured to move relative to the first skirt portion generally along the longitudinal axis of the passage. In another variation, the second skirt portion is configured to move relative to the first skirt portion generally transverse to the longitudinal axis of the passage.

In another variation, the elongate body has a medial side and a lateral side. The medial side has formed therein a cut-out portion configured to accommodate a portion of the cervical anatomy. The cut-out is configured to conform to at least one of the spinous process and the lamina of the cervical region.

In another variation, the elongate body has a configuration when inserted, e.g., positioned, within the patient, wherein the cross-sectional area of the passage at a first location is greater than the cross-sectional area of the passage at a second location, wherein the first location is distal to the second location.

In one embodiment, a retractor provides minimally invasive access to a cervical region of the spine. The retractor comprises a skirt portion having a proximal portion, a first elongate member, and a second elongate member. The skirt portion defines a passage extending therethrough through which instruments can be advanced. The first and second elongate members are configured to retract tissues to expose at least a portion of at least one cervical vertebra. The skirt portion has an expanded configuration wherein a recess is defined at least in part by at least one of the first elongate member and the second elongate member. The recess is configured to receive a portion of the cervical anatomy.

In another embodiment, an access device for exposing an upper region of the spine of a patient is provided. The access device includes a distal portion, a proximal portion, and a fastener. The distal portion has an outer surface, an inner surface partially defining a passage extending along a longitudinal axis through the access device, and an end portion configured to conform to the upper region of said spine. The proximal portion has an outer surface, an inner surface partially defining the passage, and a slot formed between the inner surface and the outer surface. The fastener is coupled with a proximal end portion of the distal portion and is configured to slide along the slot to enhance tilting of the proximal portion relative to the distal portion.

Several variations of the embodiments described above are provided below to describe other features that may be present in certain embodiments. In variations of the embodiments, one or more of the following features are included in a retractor that provides minimally invasive access to a cervical region of the spine. In one variation of the embodiments described above, the first elongate member defines a first distal end. The second elongate member defines a second distal end. The skirt portion is capable of having a low-profile configuration wherein the first and second distal ends are substantially planar. The skirt portion is capable of having an expanded configuration wherein the first and second distal ends are off-set.

In another variation, the first elongate member extends distally farther than the second elongate member when the skirt portion is in the expanded configuration. In another variation, the skirt portion is configured such that relative motion between the first elongate member and the second elongate member produces the expanded configuration. In another variation, the first elongate member is configured to translate relative to the second elongate member. In another variation, the first elongate member is configured to pivot relative to the second elongate member. In another variation, the recess is formed on a medial side of the retractor. In another variation, the passage in at least a distal portion of the retractor is defined by a cross-sectional area having a first dimension along a first axis that is greater than a second dimension along a second axis, the first axis being perpendicular to the second axis. In another variation, the recess is formed on a side of the retractor that is generally parallel to the first axis. In another variation, the retractor further comprises a proximal portion having a non-expanding configuration. In another variation, the proximal portion is oblong. In another variation, the proximal portion is circular. In another variation, the retractor is configured to enable a surgeon to view the cervical region without a viewing aid.

In one application, a method for providing treatment at or near a cervical region of the spine of a patient is provided. An incision is formed in the skin of a patient above the cervical region. An elongate body is inserted into the patient through the incision, the elongate body having a distal portion, a proximal portion, an outer surface, and an inner surface, said inner surface defining a passage extending through the elongate body. The elongate body is advanced until a distal end thereof resides at or near the cervical region of the spine. The size of the passage in the distal portion is increased relative to the size of the proximal portion.

In one application, a method for providing treatment at or near a cervical or a thoracic region of the spine of a patient is provided. An incision is formed in the skin of a patient. An elongate body is inserted into the patient through the incision. The elongate body has a distal portion, a proximal portion, an outer surface, and an inner surface. The inner surface defines a passage extending through the elongate body. The elongate body is advanced until a distal end thereof resides at or near a cervical or a thoracic region of the spine. A proximal end of the proximal portion remains outside the patient. The distal portion is configured to accommodate anatomy of the cervical or thoracic region of the spine.

Several variations of the application described above are provided below to describe other features or steps that may be present in certain applications. In variations of the application, one or more of the following are performed or included in the method for providing treatment at or near a cervical or thoracic region of the spine of a patient. In one variation of the application described above, a first implant is inserted through the elongate body to the surgical location. In another variation, a first implant is coupled with a first vertebra. In another variation, a spanning member is inserted into the elongate body. In another variation, a spanning member is coupled with a first implant and a second vertebra. In another variation, a second implant is inserted through the elongate body to the surgical location. In another variation, a second implant is coupled with a second vertebra. In another variation, a spanning member is coupled with a second implant. In another variation, a first implant is a bone screw and a spanning member is a rigid member. In another variation, a spanning member is inserted through the elongate body. In another variation, a spanning member is coupled with at least two adjacent vertebrae. In another variation, the incision is a generally cephalad-caudal incision. In another variation, the incision is formed a selected distance laterally of the spinous process of the first vertebra. In another variation, the incision is formed above the spinous process of the first vertebra. In another variation, the tissue is stripped between the incision and a location lateral of the incision. In another variation, the elongate body is advanced until the distal portion is adjacent to a lateral mass of a cervical vertebra. In another variation, the facial layer is sliced beneath the skin to facilitate advancing and configuring of the elongate body. In another variation, a procedure is performed on a spinal element at the cervical or thoracic region of the spine. Procedures that can be performed on a spinal element include a fixation, a foramenotomy, a biopsy, a tumor excision, a fusion, a motion preserving treatment, or a prosthesis deployment. In another variation, a dilating structure is inserted through the incision to widen the incision. In another variation, a dilating structure is an obturator. In another variation, a dilating structure comprises a plurality of dilators configured to progressively widen the incision.

BRIEF DESCRIPTION OF THE DRAWINGS

Further objects, features and advantages of the invention will become apparent from the following detailed description taken in conjunction with the accompanying figures showing illustrative embodiments of the invention.

Figure 1:
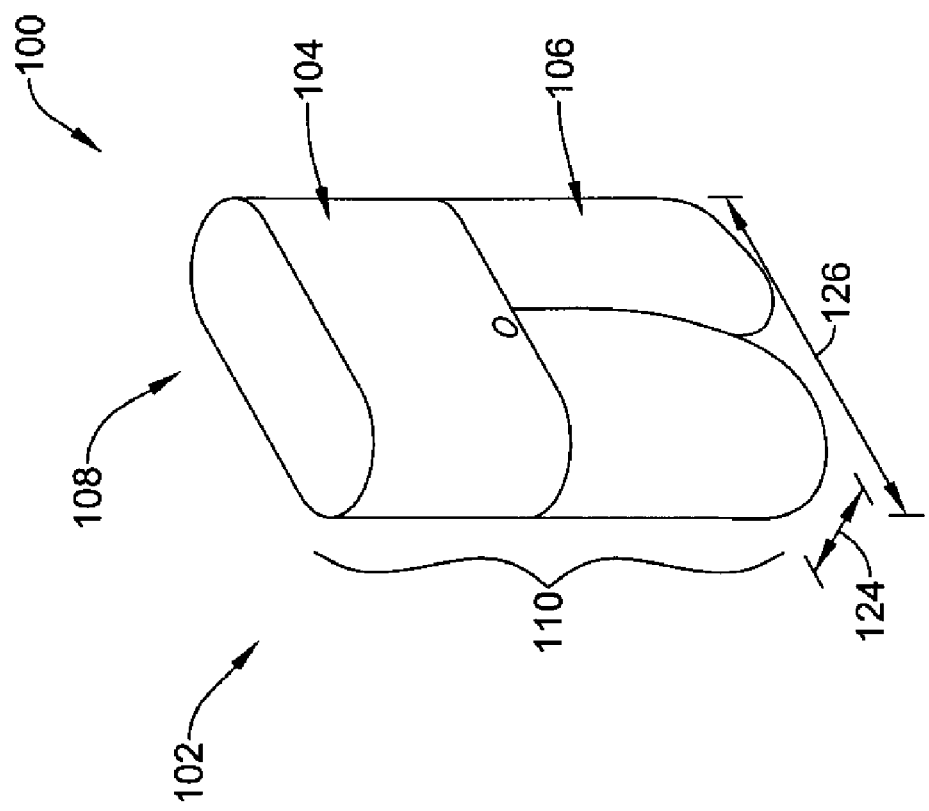
FIG. 1 is a perspective view of one embodiment of an access device adapted to provide access to an upper region, e.g., cervical regions of the spine, the access device shown in a low profile configuration.

Throughout the figures, the same reference numerals and characters, unless otherwise stated, are used to denote like features, elements, components or portions of the illustrated embodiments. Moreover, while the subject matter of this application will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENT

As should be understood in view of the following detailed description, this application is primarily directed to, though not necessarily limited to, apparatuses and methods for treating upper regions, e.g., the cervical or the thoracic region, of the spine of a patient through an access device. More particularly, the systems described below provide access to surgical locations at or near the spine and provide a variety of tools useful in performing treatment of the spine, e.g., in the cervical or thoracic region. Also, the systems described herein enable a surgeon to perform a wide variety of methods as described and incorporated by reference herein.

I. Devices for Providing Access to Upper Regions of the Spine

Various embodiments discussed below in Section I(A) include distal structures that enable the devices to be positioned adjacent or at least proximate to an upper spinal region, e.g., a cervical region. Other embodiments discussed below in connection with Section I(B) include proximal structures that generally reduce the angle of approach to a workspace adjacent to the distal end of the access devices, e.g., in an upper spinal region. Decreased angle of approach can correspond to decreased angle of insertion of an implant, making the procedures more convenient for practitioners.

Figure 2:
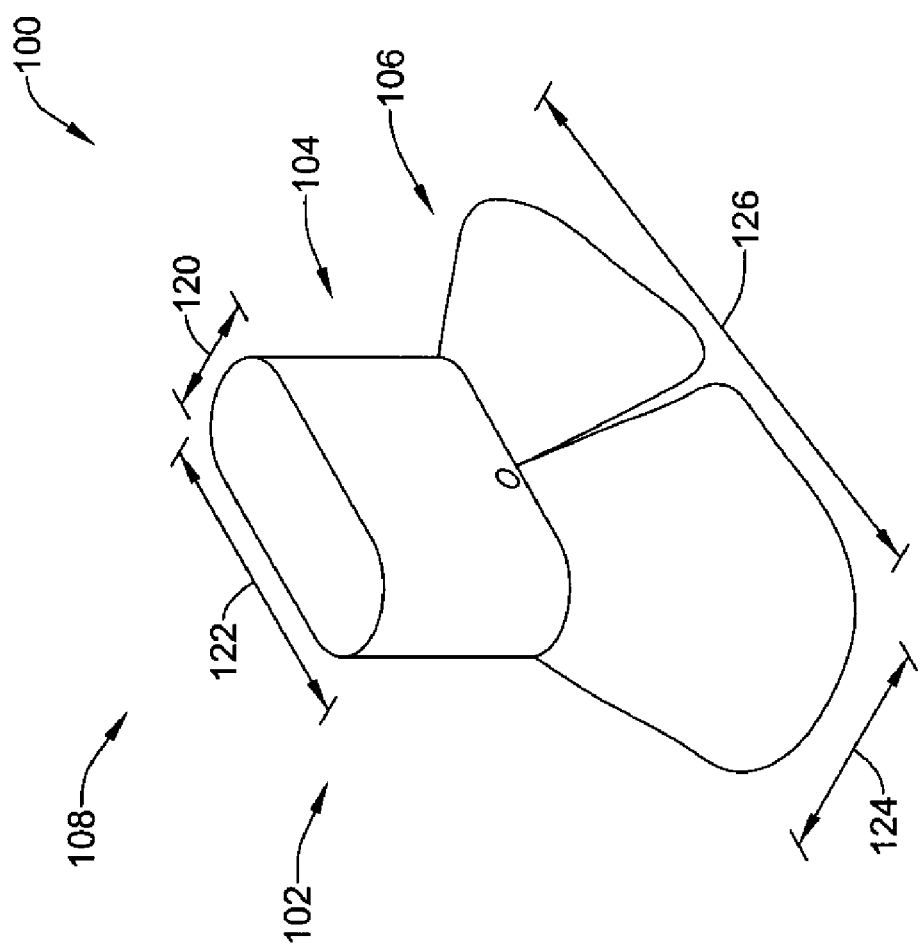
FIG. 2 is a perspective view of the access device of FIG. 1 shown in an expanded configuration.
Figure 12:
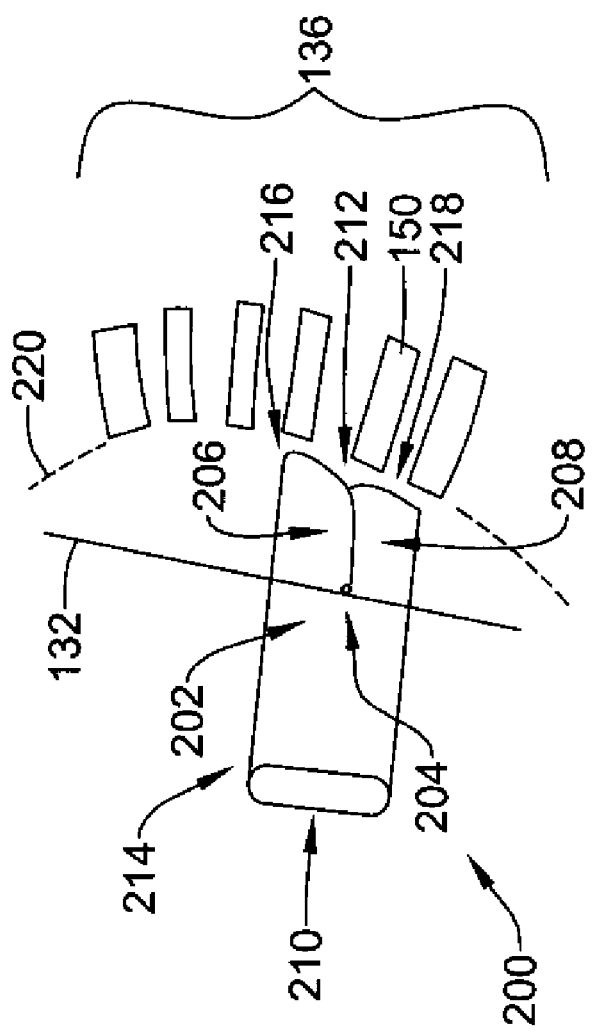
FIG. 12 is a schematic lateral view of the cervical region of the spine of a patient with one embodiment of an access device applied thereto, the access device being shown in a low profile configuration.
Figure 13:
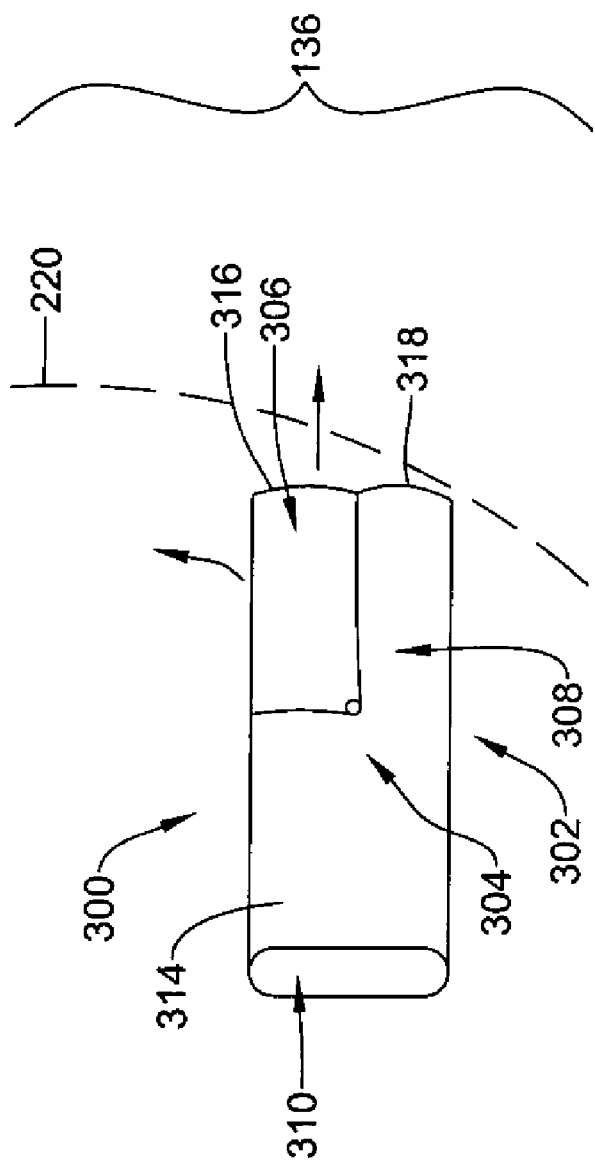
FIG. 13 is a schematic lateral view of the spine of a patient with another embodiment of an access device applied thereto, the access device being shown in a low profile configuration.
Figure 14:
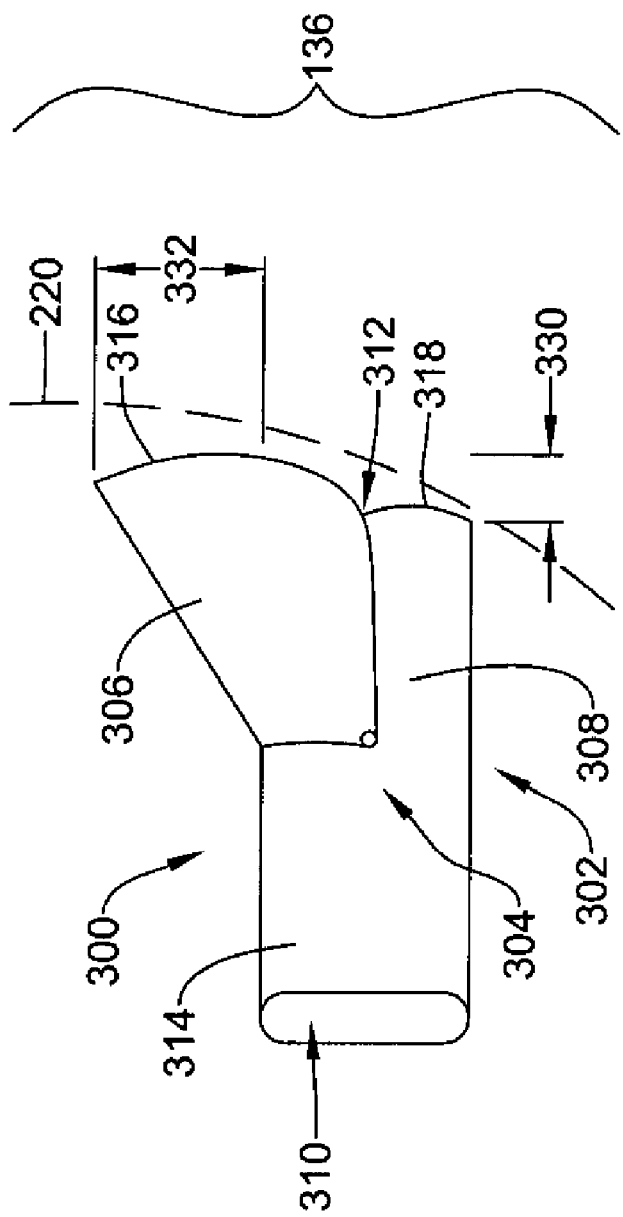
FIG. 14 is a schematic lateral view of the access device of FIG. 13 shown in an expanded configuration.
Figure 15:
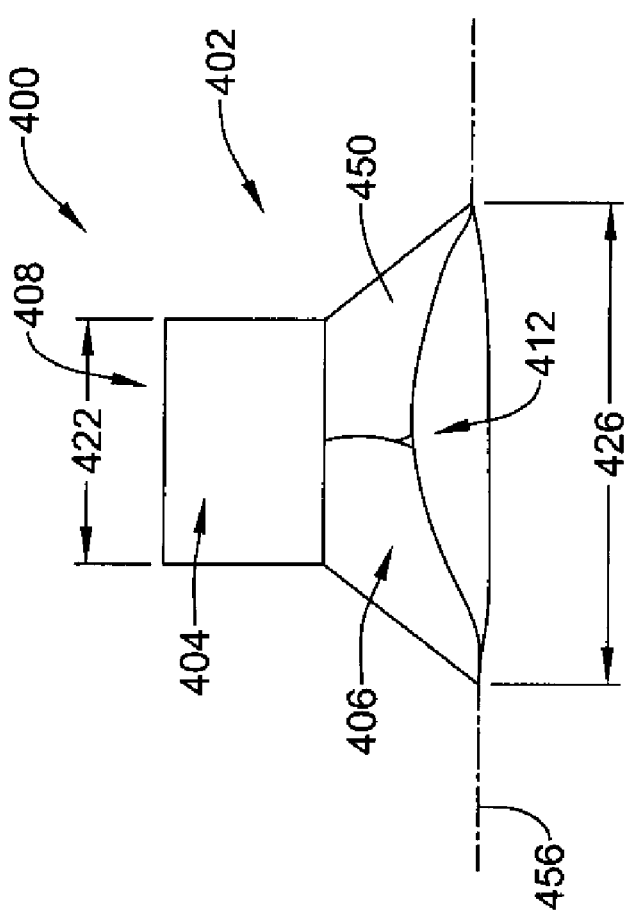
FIG. 15 is a medial side view of another embodiment of an access device capable of providing access to a cervical region of the spine, the access device being shown in an expanded configuration.
Figure 16:
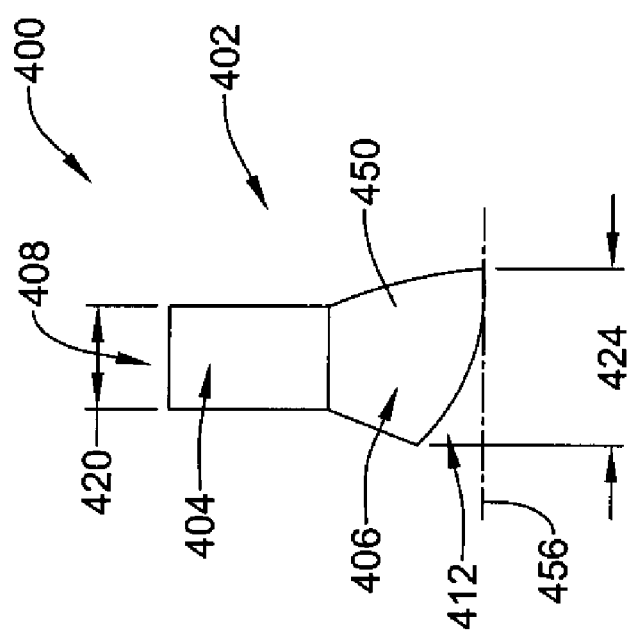
FIG. 16 is a caudal end view of the access device of FIG. 15.
Figure 17:
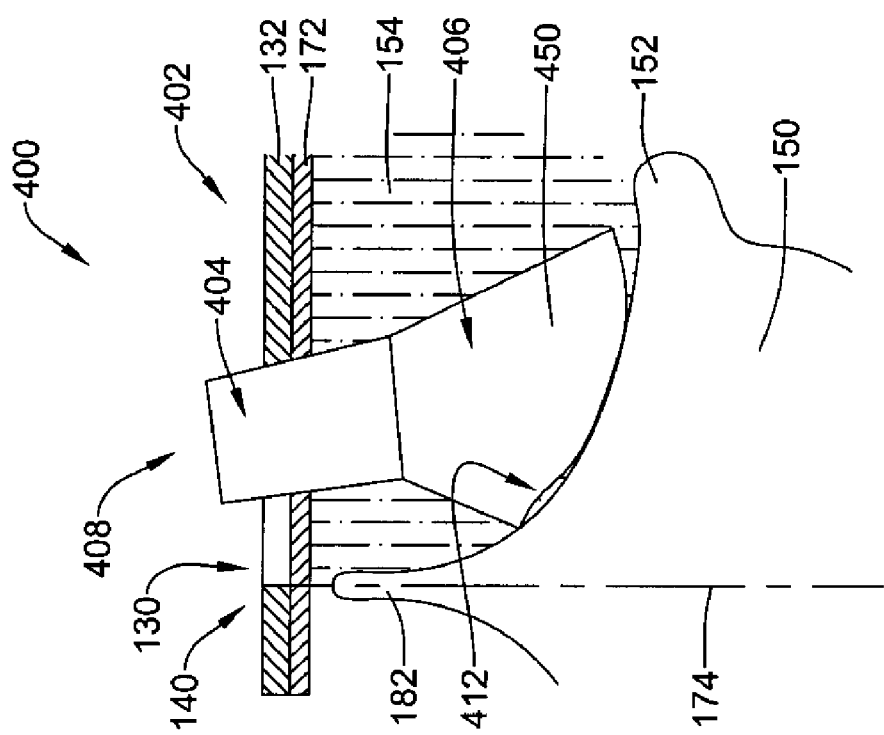
FIG. 17 is a schematic cross-sectional caudal view of the access device of FIGS. 15-16 shown applied to the patient to provide access to a region of the spine.
Figure 18:
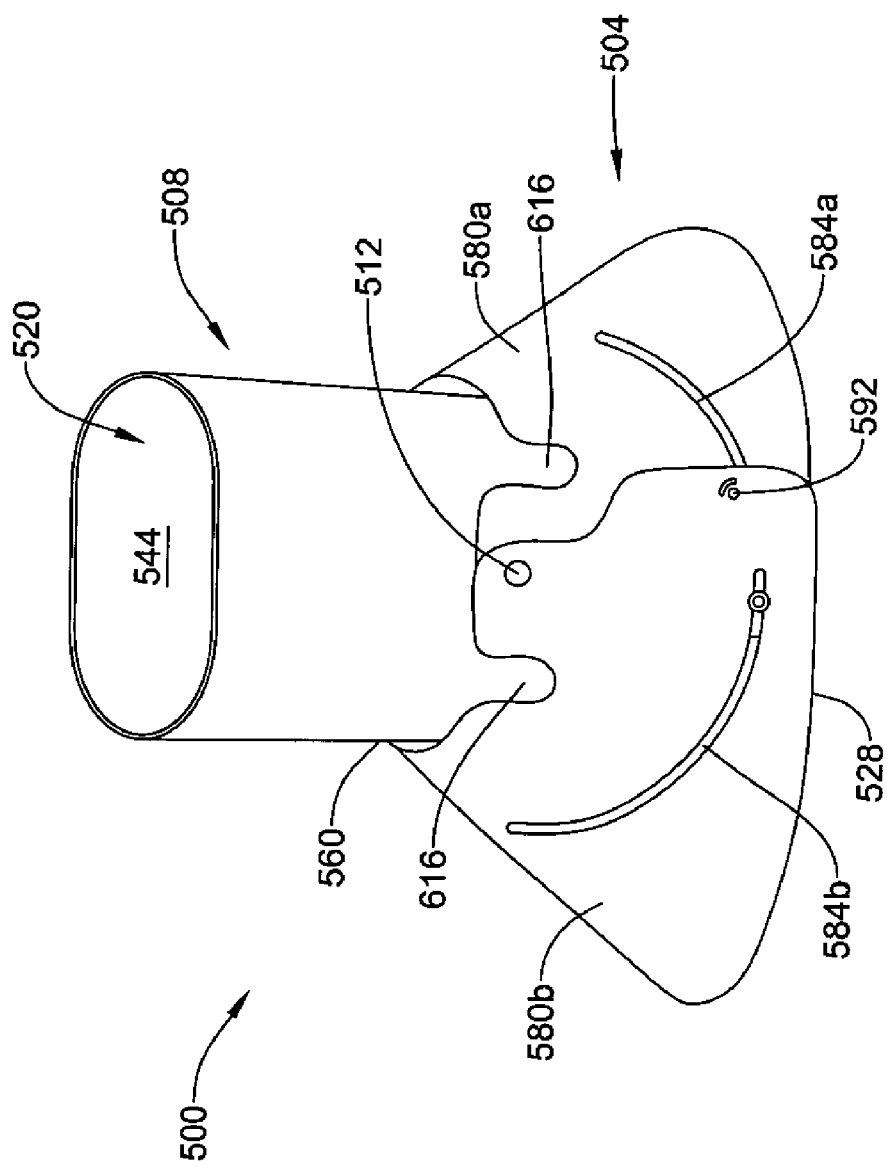
FIG. 18 is a medial side view of another embodiment of an access device.
Figure 19:
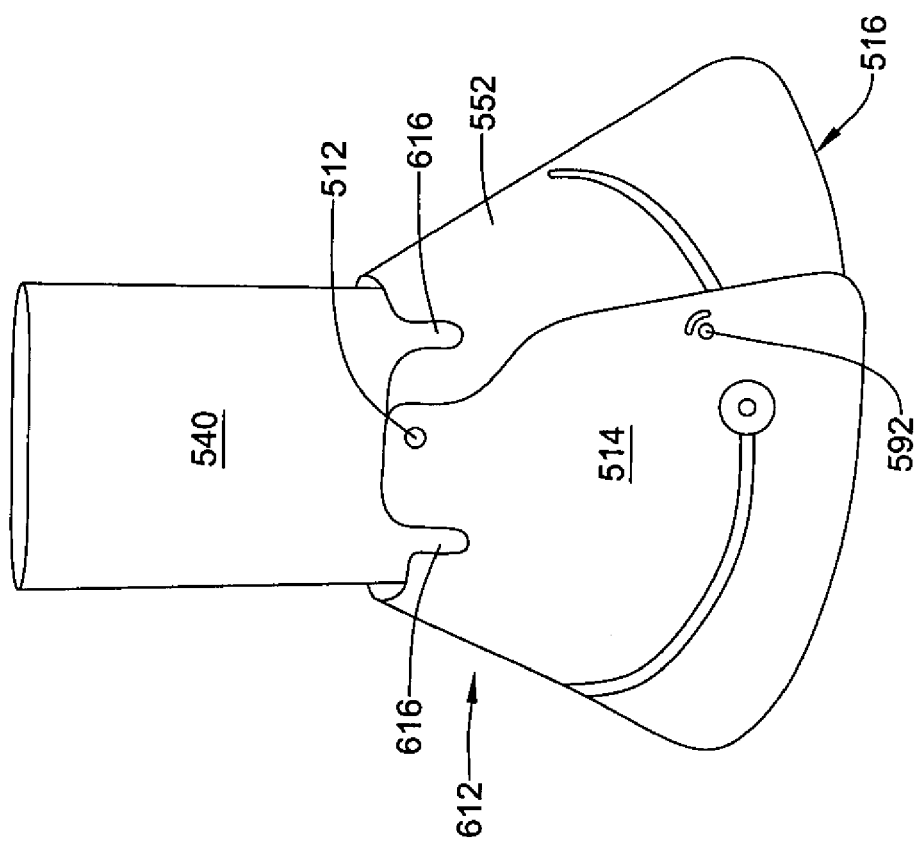
FIG. 19 is a lateral side view of the access device of FIG. 18.
Figure 20:
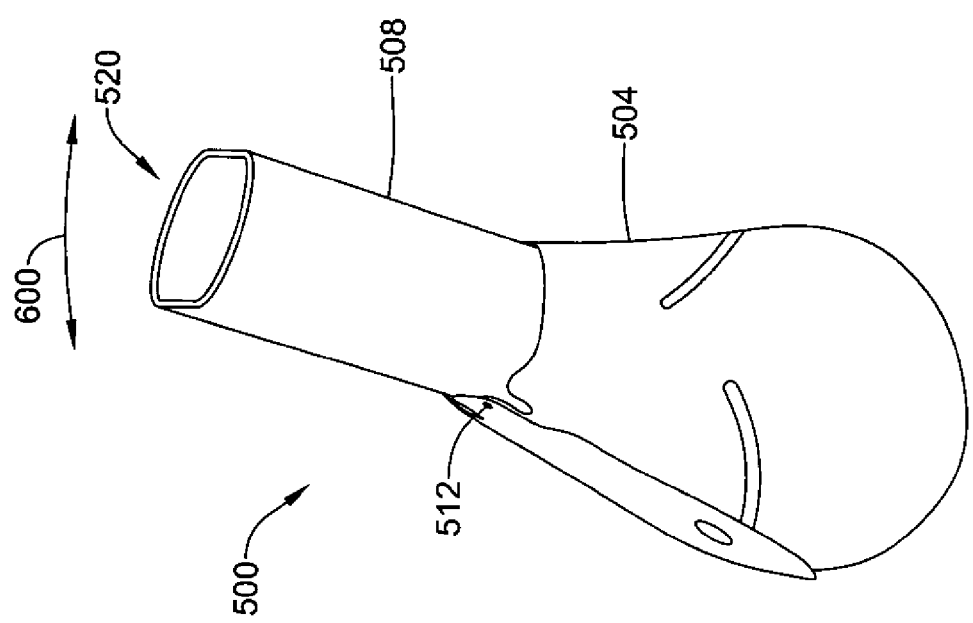
FIG. 20 is a cephalad end view of the access device of FIG. 18.
Figure 21:
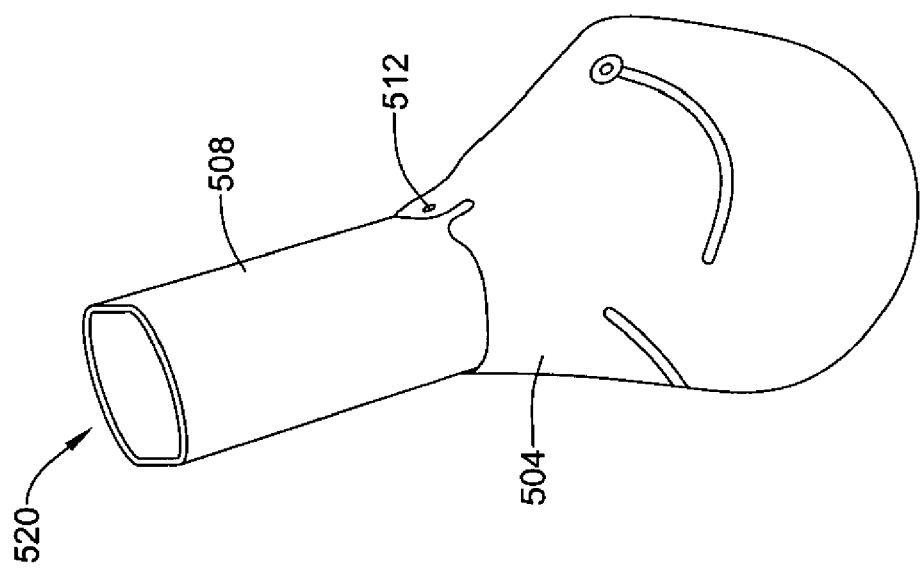
FIG. 21 is a caudal end view of the access device of FIG. 18.
Figure 22:
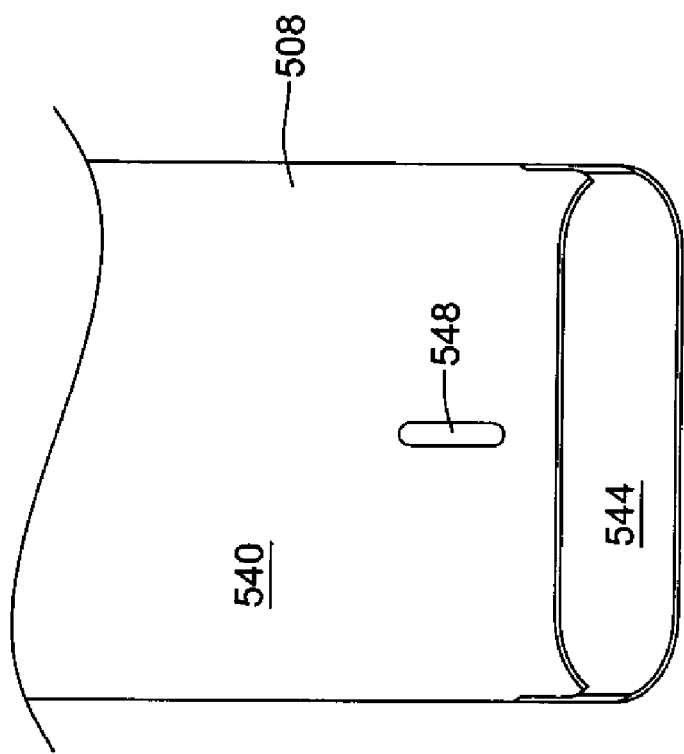
FIG. 22 is a perspective view of a distal end portion of a proximal portion of the access device of FIG. 18.

A. Access Devices Configured to be Positioned Proximate Anatomy of Upper Spinal Regions FIGS. 1-17 illustrate access devices with a variety of advantageous features for accessing upper spinal regions and techniques for such access. FIGS. 1-2 illustrate an access device 100 that is adapted to provide access to upper spinal regions, including at least on of the thoracic region and the cervical region of the spine. The access device 100 is sized to be positioned adjacent an upper region of the spine, as described further below. A variety of procedures that can be performed through the access device 100 are discussed below in connection with FIGS. 3-11. FIG. 12 illustrates another embodiment an access device 200 that is configured to conform to spinal anatomy in the cervical or other upper spinal region, as described further below. FIGS. 13-14 illustrate another embodiment an access device 300 that has a movable distal portion, enabling enhanced conformation of the access device to a spinal region. FIGS. 15-17 illustrate another embodiment an access device 400 that is configured to conform to anatomical structures between the device and the midline of the spine. FIGS. 18-24 illustrate various embodiments that are configured to enhance access to and visualization of peripheral regions of a workspace defined by the device, as well has having structures adapted to accommodate anatomy of upper spinal regions are shown below.

With reference to FIG. 1, the access device 100 is shown in a low profile configuration. The access device 100 is shown in an expanded configuration in FIG. 2. The access device 100 preferably comprises an elongate body 102 having a proximal portion 104 and a distal portion 106. The elongate body 102 defines a passage 108 extending between the proximal portion 104 and the distal portion 106, e.g., from a proximal end of the proximal portion 104 to a distal end of the distal portion 106. The overall length 110 of the access device 100 preferably is between about 30 mm and about 110 mm. In some embodiments, the overall length 110 of the access device 100 preferably is between about 50 mm and about 80 mm. In some embodiments, the overall length 110 of the access device 100 preferably is between about 60 mm and about 70 mm.

The elongate body 102 can have any suitable shape. In one embodiment, the cross-sectional shape of the elongate body 102 at one location is oblong. In some embodiments, the cross-sectional shape of the elongate body 102 at one location can be oval, elliptical, rectangular, circular, rounded, square, or other shapes.

In one embodiment having a generally circular cross-sectional shape, a proximal diameter of the elongate body 102 preferably is between about 16 mm and about 24 mm. A distal diameter of the elongate body 102 in a low profile configuration preferably is between about 16 mm and about 24 mm. The distal diameter of the elongate body 102 in an expanded configuration preferably is between about 25 mm and about 75 mm. Other circular shaped devices can be used, as appropriate for the characteristics of the procedure and patient.

In one embodiment having a generally oval and/or elliptical cross-sectional shape, a first proximal dimension 120 of the elongate body 102 preferably is between about 16 mm and about 20 mm. A second proximal dimension 122 of the elongate body 102, substantially perpendicular to the first proximal dimension 120, preferably is between about 24 mm and about 30 mm. The terms "substantially perpendicular" as used herein, can mean within about 5 degrees of perpendicular, within about 10 degrees of perpendicular, and within about 15 degrees of perpendicular for some embodiments. A first distal dimension 124 of the elongate body 102 in a low profile configuration preferably is between about 16 mm and about 20 mm. A second distal dimension 126 of the elongate body 102, substantially perpendicular to the first distal dimension 124, in a low profile configuration preferably is between about 24 mm and about 30 mm. The first distal dimension 124 of the elongate body 102 in an expanded configuration preferably is between about 18 mm and about 25 mm. The second distal dimension 126 of the elongate body 102, substantially perpendicular to the first distal dimension 124, in the expanded configuration preferably is between about 35 mm and about 75 mm. The first and second proximal dimensions 120, 122 and the first and second distal dimensions 124, 126 can be selected based on the needs of the patient, e.g., based on the procedure to be performed, on the maturity of the patient, the size of the patient, and other relevant characteristics.

The interconnection of the proximal portion 104 and the distal portion 106 can take any suitable form. For example, one or more rivets can be used to connect the distal portion 106 with the proximal portion 104. As discussed further below, in connection with certain embodiments, the interconnection of a proximal portion and a distal portion can be configured to enhance access to or viewability of a peripheral region of a surgical workspace, e.g., by increasing the range of tilting or pivoting of a proximal portion relative to a distal portion.

Figure 3:
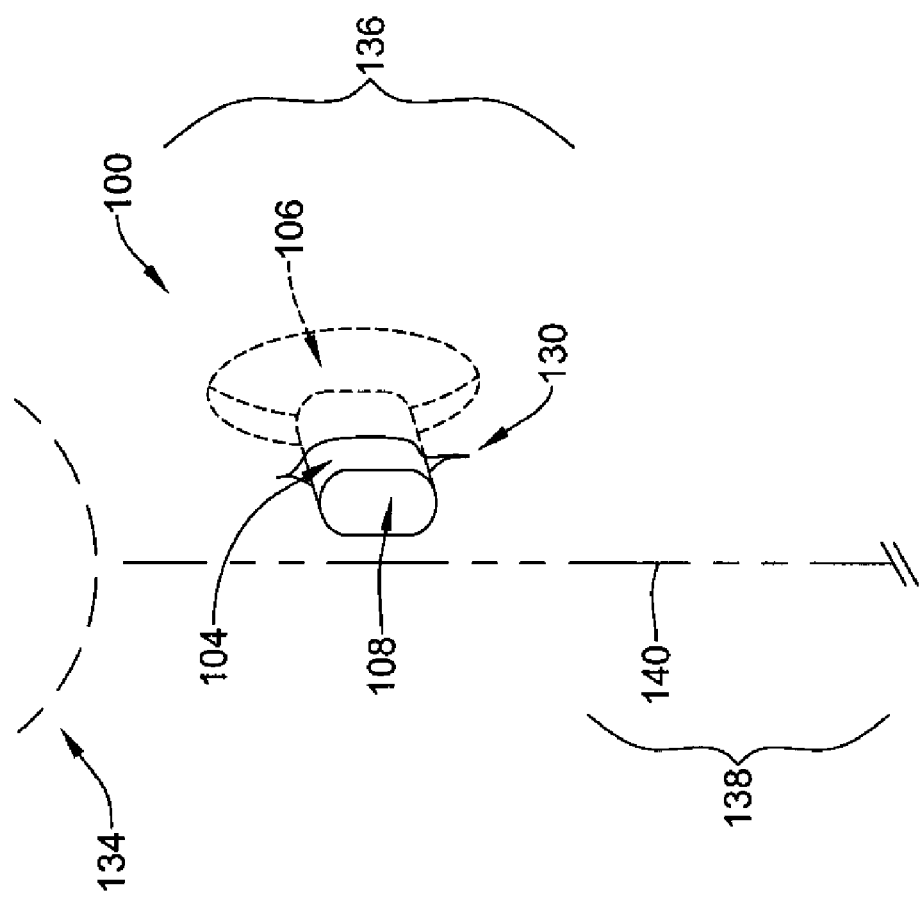
FIG. 3 is a schematic perspective view illustrating one technique for applying an access device through a cephalad-caudal incision in the skin of a patient in a cervical region of the spine of the patient.
Figure 4:
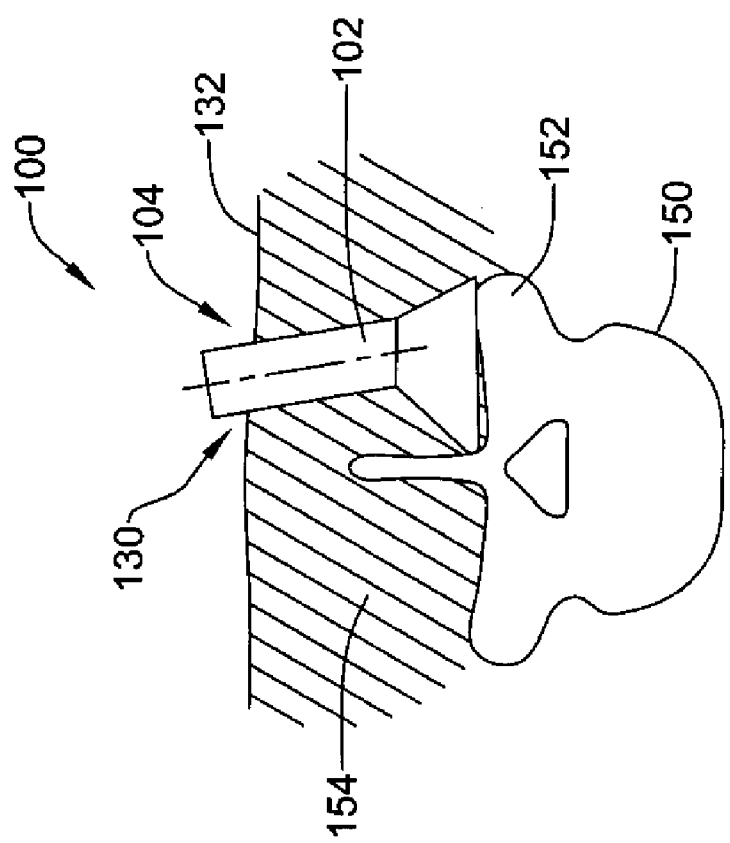
FIG. 4 is a schematic caudal view of the application of the access device shown in FIG. 3.

With reference to FIGS. 3 and 4, according to one technique for minimally invasive surgery, the access device 100 is applied through a cephalad-caudal incision 130 in the skin 132 of a patient in a cervical region of the spine of the patient. In other techniques, the access device 100 can be applied to the thoracic region of the spine.

FIG. 3 is a posterior schematic view showing the base of the skull 134, the cervical spine region 136, and the thoracic spine region 138 of the patient along a midline 140 of the spine of a patient. In the illustrated technique, the cephalad-caudal incision 130 is made at a location lateral of the midline 140. After the incision is made, the incision 130 may be further prepared prior to insertion of an access device or retractor. For example, the incision can be dilated and the tissue can be cut or stripped away if desired, as described further below. Thereafter, the access device 100 or retractor may be advanced through the incision 130, as discussed below.

After the incision is formed, the proximal portion 104 of the elongate body 102 preferably is positioned above the surface of the skin 132 and extends through the cephalad-caudal incision 130. FIG. 4 is a cross-sectional view of a stage of the technique shown in FIG. 3, showing a vertebra 150 of the cervical region of the spine, or the upper thoracic region of the spine, the lateral mass 152 of the vertebrae, the muscle tissue 154 around the vertebra 150, and the access device 100 extending above the surface of the skin 132. In the illustrated embodiment and technique, the access device 100 is in an expanded configuration. As shown in FIGS. 3 and 4, the access device 100 can be tilted or oriented such that the proximal portion 104 of the access device 100 is angled toward the midline 140 of the spine patient. This is advantageous for the cervical procedure to provide an appropriate approach angle for the anatomical structures to be accessed and the instruments to be used in the procedure. Further structures for facilitating tilting or orienting are discussed below in connection with FIGS. 18-24.

Figure 5:
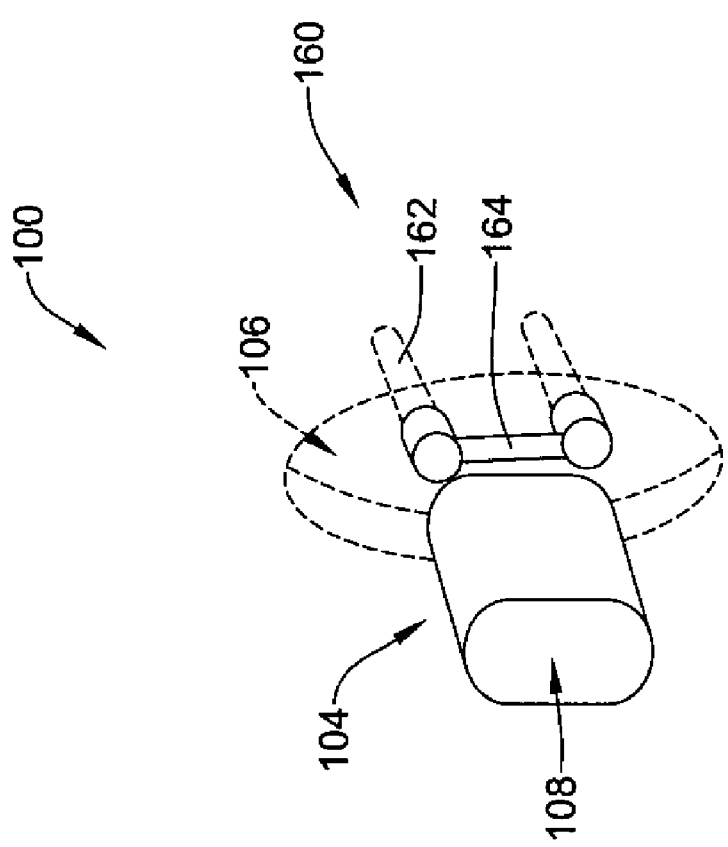
FIG. 5 is a perspective view of a proximal portion of an access device applied as shown in FIGS. 3-4 illustrating the application of a fixation assembly in a region of the spine.

With reference to FIG. 5, the access device 100 preferably is configured to provide access to the vertebrae for performing a procedure to stabilize spinal elements, such as a fixation procedure, a cervical fixation procedure, thoracic fixation procedure, or other suitable procedure. FIG. 5 shows the proximal portion 104 of the access device 100 applied as shown in FIGS. 3 and 4 illustrating the application of a fixation assembly 160 in a region of the spine.

In the illustrated technique, one or more screws 162 can be implanted into one or more lateral masses 152 of the vertebrae and one or more rods 164 can be coupled with the screws 162 to accomplish a fixation. The screws 162 preferably are top-loading tulip head screws in one technique. Other screws can also be used. Screws similar to those described in the U.S. application Ser. No. 10/483,605, filed Jan. 13, 2004, U.S. Patent Application Ser. No. 60/701,214, filed Jul. 20, 2005, and U.S. application Ser. No. 10/696,293, filed Oct. 20, 2004, each of which are hereby expressly incorporated by reference herein, can also be used.

In some embodiments, miniature versions of the screws described in these applications can be used for cervical applications. In one embodiment, the screw diameter preferably is between about 3.2 mm and about 4.5 mm. The screw lengths at the bone portion preferably are between about 10 mm and about 30 mm. In one embodiment, the rod lengths preferably are between about 15 mm and about 75 mm. The rod can be round in cross-sectional shape with diameters between about 3.0 mm and about 4.5 mm. Other suitable fixation assemblies could be applied through the access device 100. For example, a fixation assembly including one or more screws and a plate and a fixation assembly including one or more screws and a hook could be used. Other procedures not limited to fixation can also be performed through the access device 100 and the other access devices described herein. For example, a technique for treating fractures and other weakened bone portions can be performed, such as is described in U.S. patent Ser. No. 11/229/350 filed Sep. 16, 2005. Also, procedures intended to maintain at least some of the natural range of motion of the spinal region being treated can be performed through various embodiments of the devices disclosed herein. Such procedures include, but are not limited to, techniques for dynamic stabilization, as disclosed in U.S. patent application Ser. No. 10/693,815, filed Oct. 24, 2005, techniques for deploying prosthetic discs, as disclosed in U.S. application Ser. No. 10/842,651, filed May 10, 2004 and techniques for replacing a portion of a intravatribril disc, e.g., a nucleus, as disclosed in U.S. application Ser. No. 10/693,250, filed Oct. 24, 2003. The applications recited in the preceding sentence are hereby incorporated by reference herein in their entirety.

The access device 100 advantageously enables a surgeon to view the surgical location using any suitable technique, including via direct vision (with or without loupes), via a microscope, via an endoscope, and/or via any other viewing element or combinations thereof.

In other applications, the access device 100 preferably is configured to provide access to the vertebrae for performing a cervical or thoracic procedure, such as, for example, a fixation procedure using one or more screws, hooks, rods, and plates, a foramenotomy, e.g., removal of bone and/or tissue, to relieve pressure on the nerve roots and/or spinal cord, removal of tumors, and a fusion or other suitable procedure.

Figure 6:
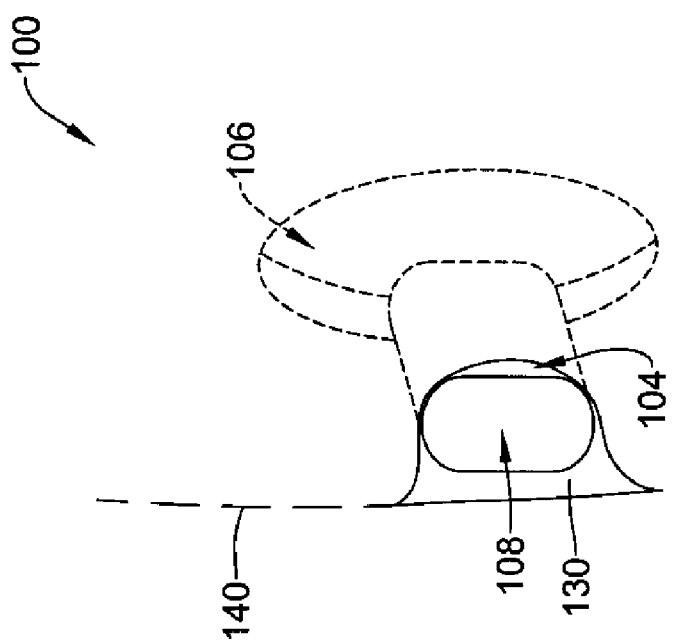
FIG. 6 is a schematic perspective view illustrating another technique for applying an access device through a cephalad-caudal incision in the skin of a patient in the cervical or the thoracic region of the spine of the patient.
Figure 7:
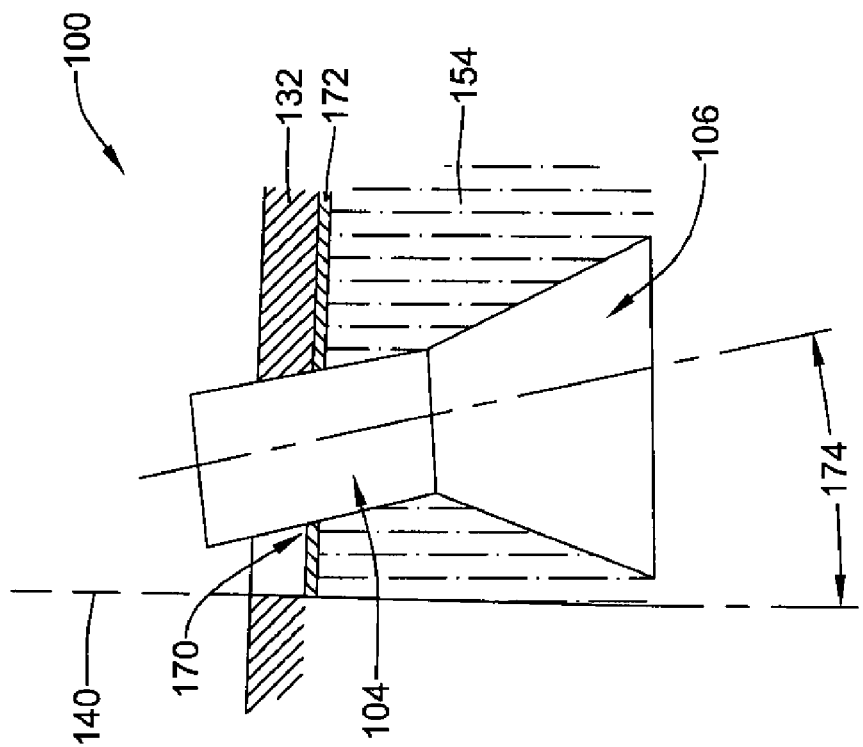
FIG. 7 is a cross-section view of the application of the access device shown in FIG. 6.

With reference to FIGS. 6 and 7, another technique is shown for applying an access device 100 through a cephalad-caudal incision 130 in the skin 132 of a patient in the cervical or the thoracic region of the spine of the patient. A single longitudinal midline incision 130 is made in the skin 132 of the patient. The skin 132 is dilated laterally and another incision 170 is made in the fascial layer 172 and muscle 154 to receive the access device 100. As shown in FIGS. 6 and 7, the access device 100 can be tilted or oriented such that the access device 100 is angled relative to a plane 174 extending through the midline 140 of the patient by an angle 174 of between about 0 degrees and about 30 degrees. Larger angles of tilt are advantageous for accessing peripheral areas of a workspace defined within the access device 100, e.g., lateral portions of the spinal anatomy, while smaller angles of tilt are advantageous for accessing medial portions of the spinal anatomy. Further features for enhancing the tiltability of an access device, such as the access device 100, are discussed below in connection with FIGS. 18-24.

Figure 8:
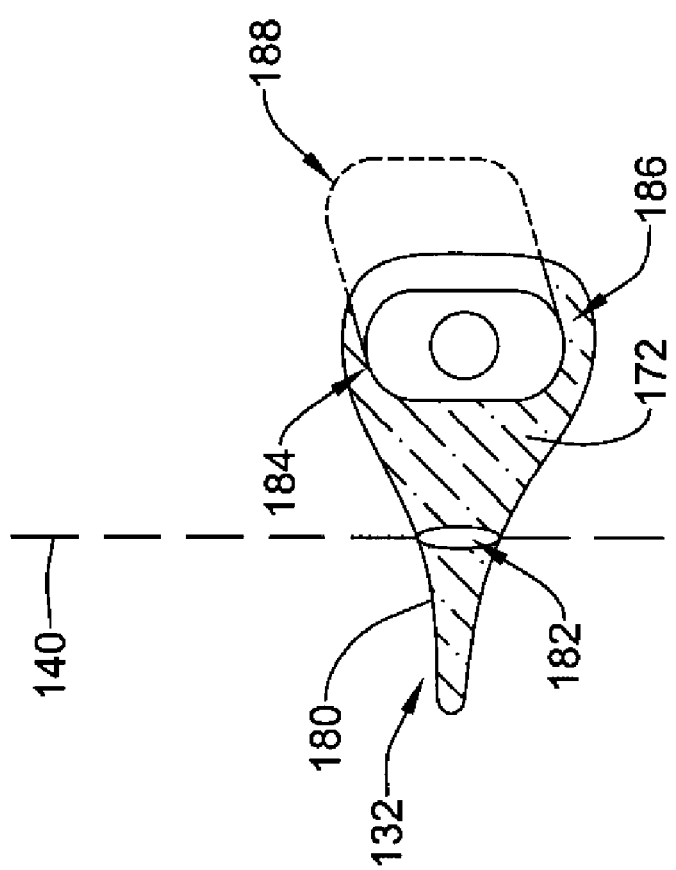
FIG. 8 is a schematic perspective view illustrating a technique for applying a dilating structure through a medial-lateral incision in the skin of a patient in a region of the spine of the patient.
Figure 9:
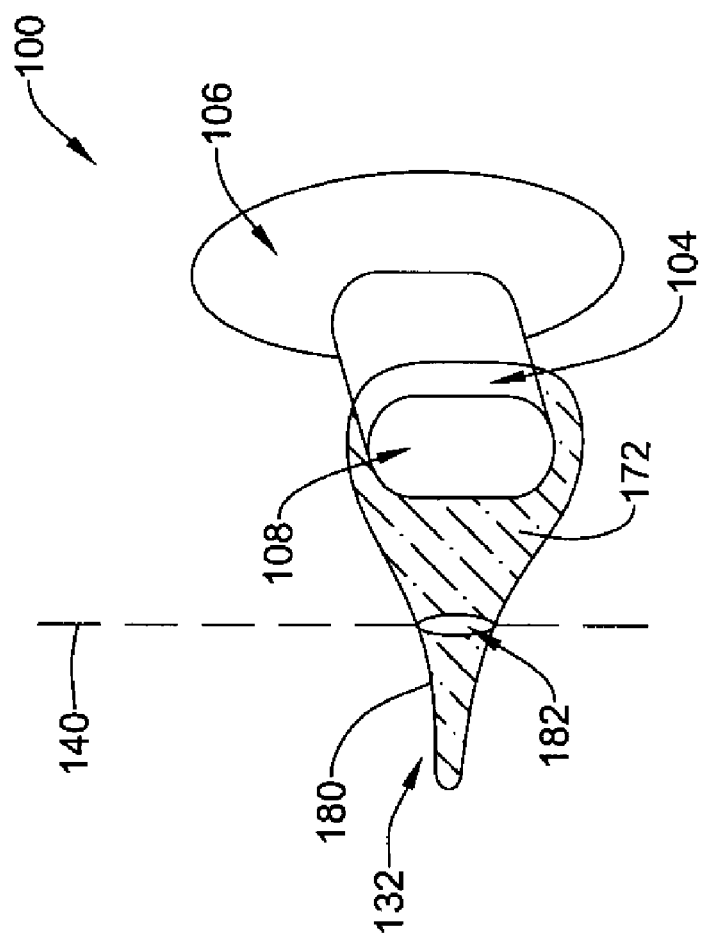
FIG. 9 is a schematic perspective view illustrating a technique for applying an access device through a medial-lateral incision in the skin of a patient in a region of the spine of the patient.

With reference to FIGS. 8 and 9, one technique is shown for applying an access device 100 through a transverse incision 180 in the skin 132 of a patient in the cervical or the thoracic region of the spine of the patient. A single incision 180 is made in the skin 132 transverse to the midline 140 of the patient, e.g., extending generally perpendicular to the midline 140 on one or both sides of the midline 140. Such an incision might expose a vertebral structure, such as a spinous process 182 of a vertebra, as is illustrated schematically in FIGS. 8 and 9 along the midline 140 of the patient. The skin incision 180 is dilated longitudinally, e.g., in the cephalad-caudal direction, and one or more incisions 184, 186 are made laterally from the midline 140 in the fascial layer 172 and muscle 154 to receive the access device 100. In one technique, the facial incisions 184, 186 are made in the longitudinal, e.g., cephalad-caudal, direction to permit easier retraction and/or expansion by the access device 100 and increase resultant exposure of the spine.

The fascial layer 172 may be dilated using sequential dilators or a single dilator or obturator 188. The dilator or obturator 188 can be placed through the single transverse skin incision 180 and through the one or more fascial incisions 184, 186 on one side of the spine. The access device 100 is applied to the patient over the dilator or obturator 188. The dilator or obturator 188 is removed and the access device 100 is expanded to retract tissue. In one technique an expandable dilator is used to increase the size of an incision, such as the incision 180. Expandable dilators are discussed in U.S. Provisional Application No. 60/630,180, filed Nov. 22, 2004, which is hereby incorporated by reference herein.

FIG. 9 shows that the access device 100 can be tilted or oriented such that the access device 100 is angled relative to a plane extending through the midline 140 of the patient. In some techniques, the skin incision 180 is again dilated longitudinally, e.g., in the cephalad-caudal direction, and one or more incisions are made laterally from the midline 140 in the fascial layer 172 and muscle 154 on the other side of the spine to receive an access device 100 to provide access to the other side of the vertebrae through the single transverse skin incision 180.

Figure 10:
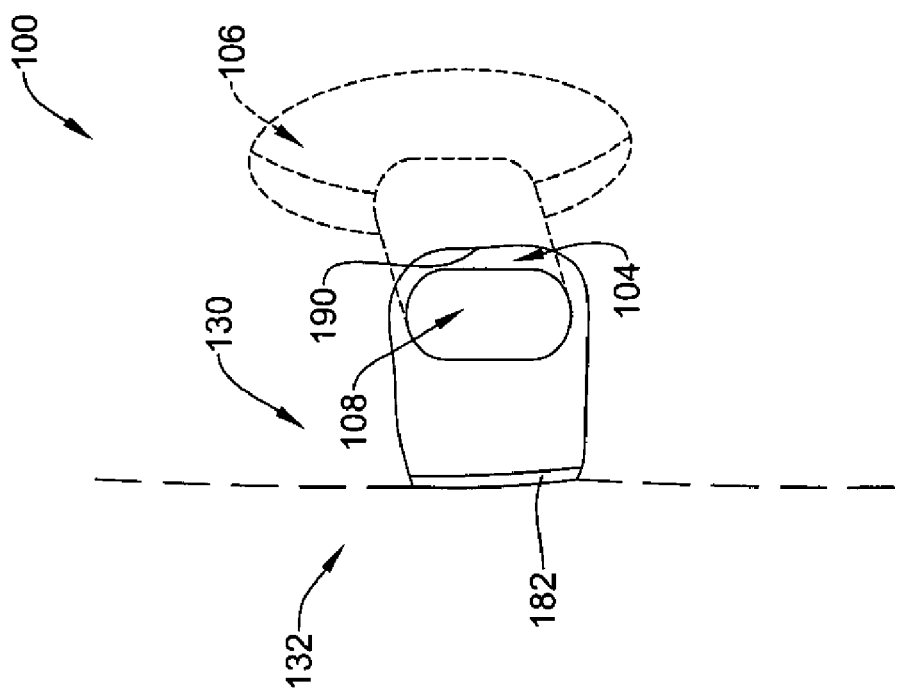
FIG. 10 is a schematic perspective view illustrating another technique for applying an access device through a cephalad-caudal incision in the skin of a patient in a region of the spine of the patient.
Figure 11:
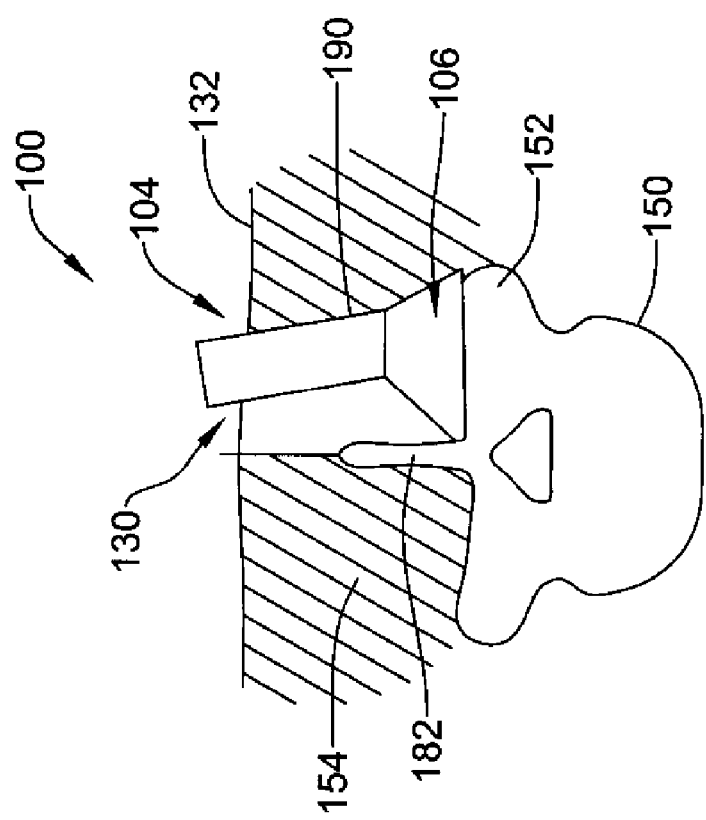
FIG. 11 is a schematic caudal view of the application of the access device shown in FIG. 10.

FIGS. 10 and 11 illustrate another technique for applying an access device 100 through an incision 130 in the skin 132 of a patient in the cervical or the thoracic region of the spine of the patient. The incision 130 is made in the skin 132 of the patient. Muscle 154 is stripped laterally off the spinous process 182 and bony anatomy. A cobb, dilator, or other instrument can be used to strip the tissue, e.g., muscle 154, away from the bony anatomy. Cobb device that could be used to ease insertion of the access devices described herein are discussed in U.S. application Ser. No. 10/935,574, filed Sep. 7, 2004, which is hereby incorporated by reference herein in its entirety. The access device 100 preferably is positioned within the patient. The stripped tissue, e.g., the muscle 154, is retracted between the spinous process 182 and a lateral edge of the access device 100, e.g., from the spinous process 182 to the lateral edge 190 of the expandable access device 100.

The access device 100 can be adapted to include other convenient features, such as any of those described in 10/972, 987, filed Oct. 25, 2004, which is hereby incorporated by reference herein.

With reference to FIG. 12, in another embodiment, an access device or retractor 200 is adapted to provide access to a cervical and/or thoracic region of the spine. The access device 200 is similar to other access devices described herein, except as set forth below. FIG. 12 is a schematic lateral view of the cervical region 136 of the spine of a patient with the access device 200 applied thereto. The retractor 200 is configured to conform to the anatomy of an upper region of the spine, e.g., the cervical region 136. The retractor 200 is shown in a low profile configuration in FIG. 12. The retractor 200 is capable of being positioned in an expanded configuration, as discussed below.

The retractor 200 comprises a skirt portion 202 having a proximal portion 204, a first elongate member 206, and a second elongate member 208. The skirt portion 202 defines a passage 210 extending therethrough through which instruments can be advanced. The first and second elongate members 206, 208 are configured to retract tissues to expose at least one cervical vertebra. The skirt portion 202 has an expanded configuration wherein a recess 212 is defined at least in part by the first elongate member 206 and the second elongate member 208. The recess 212 is configured to receive or accommodate a portion of the cervical anatomy.

FIG. 12 shows that in one embodiment, the retractor 200 comprises a proximal portion 214 that has a non-expanding configuration. The access devices and retractors disclosed herein, including the retractor 200, can be configured with an expandable proximal portion as illustrated in U.S. application Ser. No. 10/845,389, filed May 13, 2004, which is hereby incorporated by reference herein. In one embodiment, the proximal portion 214 is oblong. In another embodiment, the proximal portion 214 is circular. The retractor 200 preferably is configured to enable a surgeon to view the cervical region without a viewing aid.

The first elongate member 206 defines a first distal end 216. The second elongate member 208 defines a second distal end 218. With reference to FIG. 12, the skirt portion 202 is capable of having a low-profile configuration wherein the first and second distal ends 206, 208 are off-set. The skirt portion 202 preferably is capable of having an expanded configuration wherein the first and second distal ends 206, 208 are off-set. For example, the first elongate member 206 extends distally farther than the second elongate member 208 when the skirt portion 202 is in the expanded configuration.

The first elongate member 206 and the second elongate member 208 preferably cooperate to conform, or substantially conform, to spinal anatomy, e.g., by conforming or substantially conforming, when deployed, to the lordosis 220 of the spine. As used herein, the term "conforming" includes substantially conforming, and "substantially conforming" is a broad term, and includes having a shape that enables the access device to be positioned close enough to the anatomy to substantially prevent tissue encroachment into the passage of the access device. The terms "substantially prevent tissue encroachment" can mean confining tissue encroachment to the outer 5% of the surgical space along the perimeter in some procedures, the outer 10% of the surgical space along the perimeter in other procedures, and the outer 20% of the surgical space along the perimeter in other procedures.

In some embodiments, the first elongate member 206 of the skirt 202 may be between about 10 mm and about 30 mm longer than the second elongate member 208 of the skirt 202. The passage 210 in at least a distal portion of the retractor 200 is defined in some embodiments by a cross-sectional area having a first dimension along a first axis that is greater than a second dimension along a second axis, the first axis being perpendicular to the second axis.

FIGS. 13 and 14 illustrate another embodiment of an access device or retractor 300 that is adapted to provide access to a cervical and/or thoracic region of the spine. The retractor 300 is similar to other access devices described herein, except as set forth below. FIG. 13 is a schematic lateral view of the spine of a patient with the retractor 300 applied thereto. The retractor 300 is shown in a low profile configuration. FIG. 14 shows the retractor 300 in an expanded configuration. The retractor 300 is configured to conform to the anatomy of the cervical region 136 of the spine.

The retractor 300 comprises a skirt portion 302 having a proximal portion 304, a first elongate member 306, and a second elongate member 308. The skirt portion 302 defines a passage 310 extending therethrough through which instruments can be advanced. The first and second elongate members 306, 308 are configured to retract tissues to provide access to at least a portion of at least one cervical vertebra. The skirt portion 302 has an expanded configuration wherein a recess 312 is defined at least in part by the first elongate member 306 and the second elongate member 308. The recess 312 is configured to receive a portion of the cervical anatomy.

As shown in FIGS. 13 and 14, the retractor 300 comprises a proximal portion 314 having a non-expanding configuration in one embodiment. Other embodiments have expandable proximal portions, as discussed above. In one embodiment, the proximal portion 314 is oblong. In another embodiment, the proximal portion 314 is circular. The retractor 300 preferably is configured to enable a surgeon to view the cervical region 136 without a viewing aid, though viewing aids can be used if needed.

The first elongate member 306 defines a first distal end 316. The second elongate member 308 defines a second distal end 318. With reference to FIGS. 13 and 14, the skirt portion 302 is capable of having a low-profile configuration wherein the first and second distal ends 306, 308 are substantially planar, e.g., at about the same depth beneath the skin. The skirt portion 302 preferably is capable of having an expanded configuration wherein the first and second distal ends 306, 308 are off-set. For example, the first elongate member 306 extends distally farther than the second elongate member 308 when the skirt portion 302 is in the expanded configuration. The skirt portion 302 is configured such that relative motion between the first elongate member 306 and the second elongate member 308 produce the expanded configuration. The first elongate member 306 and the second elongate member 308 preferably cooperate to conform to spinal anatomy, e.g., lordosis 220 of the spine, when deployed. The first elongate member 306 preferably is configured to translate relative to the second elongate member 308.

In some embodiments, the first elongate member 306 of the skirt 302 can translate relative the second elongate member 308 an amount 330 such that the first elongate member 306 is between about 10 mm and about 30 mm longer than the second elongate member 308 in the expanded configuration. The first elongate member 306 preferably is configured to pivot relative to the second elongate member 308. In some embodiments, the first elongate member 306 pivots relative the second elongate member 308 an amount 332 to expand the passage 310 of the skirt 302 by between about 10 mm and about 50 mm. The passage 310 in at least a distal portion of the retractor 300 is defined by a cross-sectional area having a first dimension along a first axis that is greater than a second dimension along a second axis, the first axis being perpendicular to the second axis.

With reference to FIGS. 15 and 16, in another embodiment, an access device 400 is adapted to provide access to a cervical region of the spine. The access device 400 is similar to other access devices described herein, except as set forth below. A medial side view of the access device 400 in an expanded configuration is shown in FIG. 15. An end view of the access device 400 is shown in FIG. 16. The access device 400 preferably comprises an elongate body 402 having a proximal portion 404 and a distal portion 406. The elongate body 402 defines a passage 408 extending from the proximal portion 404 to the distal portion 406. The elongate body 402 can have any suitable shape.

In one embodiment having a generally oblong, e.g., oval or elliptical, cross-sectional shape, a first proximal dimension 420 of the elongate body 402 preferably is between about 16 mm and about 20 mm. A second proximal dimension 422 of the elongate body 402, substantially perpendicular to the first proximal dimension 420, preferably is between about 24 mm and about 30 mm. A first distal dimension 424 of the elongate body 402 in a low profile configuration preferably is between about 16 mm and about 20 mm. A second distal dimension 426 of the elongate body 402, substantially perpendicular to the first distal dimension 424, in a low profile configuration preferably is between about 24 mm and about 30 mm. The first distal dimension 424 of the elongate body 402 in an expanded configuration preferably is between about 18 mm and about 25 mm. The second distal dimension 426 of the elongate body 402, substantially perpendicular to the first distal dimension 424, in the expanded configuration preferably is between about 35 mm and about 75 mm.

The access device 400 is configured to conform to the anatomy of the cervical region of the spine. The access device 400 is shown in an expanded configuration. Preferably, the access device 400 has a contracted configuration that facilitates insertion into a patient using a technique similar to those discussed above. The access device 400 comprises a skirt portion 450. The skirt portion 450 at least partially defines in the passage 408 through which instruments can be advanced. The skirt portion 450 is configured to retract tissues to expose at least one cervical vertebra 150. The skirt portion 450 has an expanded configuration wherein a recess 412 is defined. The recess 412 is configured to receive a portion of the cervical anatomy.

In one embodiment, the recess 412 is formed on a medial side of the elongate body 402. The passage 408 in at least a distal portion 406 of the elongate body 402 is defined by a cross-sectional area having a first dimension along a first axis 456 that is greater than a second dimension along a second axis 454, the first axis 456 being generally perpendicular to the second axis 454. The recess 412 is formed on a side of the elongate body 402 that is generally parallel to the first axis 456, e.g., on of the sides of the elongate body 402 that is not intersected by the first axis 456.

With reference to FIG. 17, according to another technique for minimally invasive surgery, the access device 400 is applied through an incision 130 in the skin 132 of a patient in a cervical region of the spine of the patient. In other techniques, the access device 400 can be applied to the thoracic region of the spine. In the illustrated technique, the incision 130 is made along a midline 140 of the patient. At least part of the proximal portion 404 of the elongate body 402 preferably is positioned above the surface of the skin 432 and extends through the incision 430. FIG. 17 is a cross-sectional view showing the vertebrae 150 of the cervical spine, or upper thoracic spine, the lateral mass 152 of the vertebrae 150, the muscle tissue 154, the fascial layer 172, the skin 132, and the access device 400 extending above the surface of the skin 432. In the illustrated technique, the access device 400 is expanded to the expanded configuration. As shown in FIG. 17, the access device can be tilted or oriented such that the proximal portion 404 of the access device 400 is angled toward a plane 174 passing through the midline 140 of the patient. The distal portion 406 of the skirt 450 on the medial side has a cutout 412 to conform to the bony anatomy, e.g., one or more of the spinous process 182, lamina, and any bony structure between the lateral mass and spinous process.

B. Access Devices Configured to Enhance Access to Peripheral Regions of a Surgical WorkSpace As discussed further below, in connection with certain embodiments, an interconnection of a proximal portion and a distal portions can be configured to enhance tilting or pivoting of the proximal portion relative to the distal portion.

FIGS. 18-22 illustrate another embodiment of an access device 500 wherein tilting, pivoting, or movement of a proximal portion relative to a distal portion is enhanced. The access device 500 is similar to those hereinbefore described, except as set forth below.

As discussed further below, the access device 500 is useful for exposing an upper region of the spine of a patient. The access device includes a distal portion 504, a proximal portion 508, and a fastener 512. The distal portion 504 has an outer surface 514, an inner surface 516 partially defining a passage 520 extending along a longitudinal axis through the access device 500. The access device 500 also has an end portion configured to conform to the upper region of the spine. As discussed above, the upper region can be a cervical region of the spine. The upper region also can be a thoracic region of the spine. The end portion can be configured to confirm in manner similar to the devices disclosed hereinabove or in any of the applications incorporated by reference herein. For example, the distal portion 504 can have a recess defined by a lower, medial edge 528 of the distal portion 504. The recess is similar to the recess 412, discussed above.

The proximal portion 508 has an outer surface 540, an inner surface 544 that partially defines the passage 520, and a slot 548 formed between the inner surface 544 and the outer surface 540. The fastener 512 is coupled with a proximal end portion 552 of the distal portion 504 and is configured to slide along the slot 548 to enhance tilting, e.g., of the proximal portion 508 relative to the distal portion 504.

In one embodiment, a second fastener 560 joins the proximal end portion 552 of the distal portion 504 to the proximal portion 508 at a second location, e.g., on a side of the access device 500 that is opposite the slot 548. The second fastener 560 can take any suitable form, e.g., a rivet or other fastener that is configured to restrict motion. The second fastener 560 can be coupled with the proximal portion 508 by way of a slot similar to the slot 548.

Other features of the access device can be similar to some of those described above or in the documents incorporated by reference herein. For example, the distal portion 504 can be configured as a skirt portion that has a caudal half portion 580a and a cephalad half portion 580b. The caudal and cephalad half portions 580a, 580b can be configured to reside on the caudal and cephalad sides of the access device 500 when the device is applied and to retract tissue between the device and the caudal and the cephalad ends of the body respectively. The caudal and cephalad half portions 580a, 580b can be configured with slots 584a, 58b on either side or both the medial and the lateral sides of the device 500 to facilitate opening and closing of the device. In some embodiments, a locking device 592 is useful for keeping the access device in a selected configuration, e.g., a fully open configuration. In the illustrated embodiment, two locking devices are provided, one on the medial side and one on the lateral side of the device 500.

In use, the access device 500 can be applied laterally of the spinous process, as discussed above. In this position, the passage preferably is between the slot 548 and the midline of the spine. The slot 548 enables the proximal portion 508 to tilt relative to the distal portion 540, as illustrated by the arrow 600 in FIG. 20. In one embodiment, the coupling of the proximal and distal portions 508, 504 at the slot 548 is arranged such that in a relaxed state the fastener 512 is at the lower, e.g., distal, end of the slot 548. The proximal portion 508 can then be urged distally so that the fastener 512 moves toward the upper, e.g., proximal, end of the slot 548. When in this position, a region of the workspace that is closer to the midline of the spine is directly below the projection of the upper, e.g., proximal end of the proximal portion 508. This results in a more direct line of access to that region of the workspace. The slot 548 is arranged along a longitudinal axis that is parallel to the longitudinal axis of the passage 520. This arrangement increases the range of positions in the workspace, including peripheral regions, that are more directly accessible beneath a projection of the proximal end of the proximal portion 508. More direct access makes the procedure easier because it increases visibility of the site and increases the ability of practitioners to perform more procedures through the device 500.

Another feature found in some variations of the access device 500 is a structure 612 configured to reduce the stiffness of the device, e.g., near a junction of the proximal portion 508 and of the distal portion 504. The structure 612 can take any suitable form, such as including one or more cutouts 616 that reduce the stiffness of the distal portion 504. Reducing the stiffness of the distal portion reduces the resistance of the access device 500 to tilting and other adjustments along the slot 548, thereby making it easier for a surgeon to reposition the proximal portion, increasing access to peripheral regions of the working space. Although four cutouts 616 are shown, other embodiments can have one, two, three, or more than three cutouts. Also, five or more cutouts 616 can be provided. In addition, other shapes and configurations of the cutout 616 can be provided.

Figure 23:
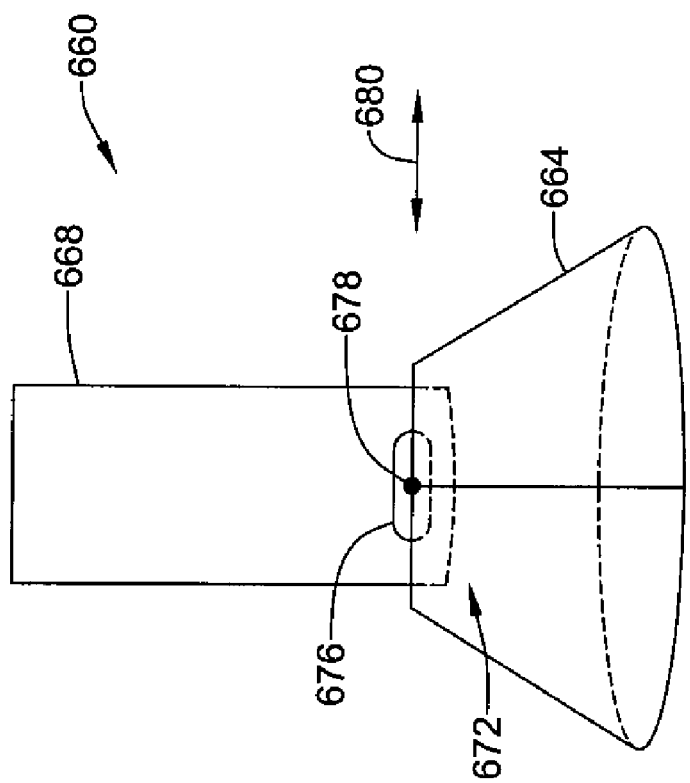
FIG. 23 is a side view of another embodiment of an access device.

FIG. 23 illustrates another embodiment of an access device 660 that is configured for increased access to peripheral regions of a workspace, where the peripheral regions are primarily at one or both of the cephalad and caudal ends of the workspace. In the illustrated embodiment, the access device 660 has a distal portion 664 and a proximal portion 668. The distal and proximal portions 664, 668 are joined at a junction 672 that enables relative movement therebetween. For example, a slot 676 can be formed at the junction 672, e.g., in one of the distal and proximal portions 664, 668. A fastener 678 can be rigidly coupled with the other of the distal and proximal portions 664, 668 and slidably coupled with the slot 676. As illustrated by the arrow 680, the junction 672 enables relative movement along an axis that would be generally parallel with a cephalad-caudal axis of the patient when applied to a patient. Such movement enables better visualization of and access to a peripheral region of the workspace, particularly in the cephalad and caudal peripheral regions, as discussed above. As such, implants and instruments can be more easily inserted to the workspace and positioned to engage the spinal region being treated.

Figure 24:
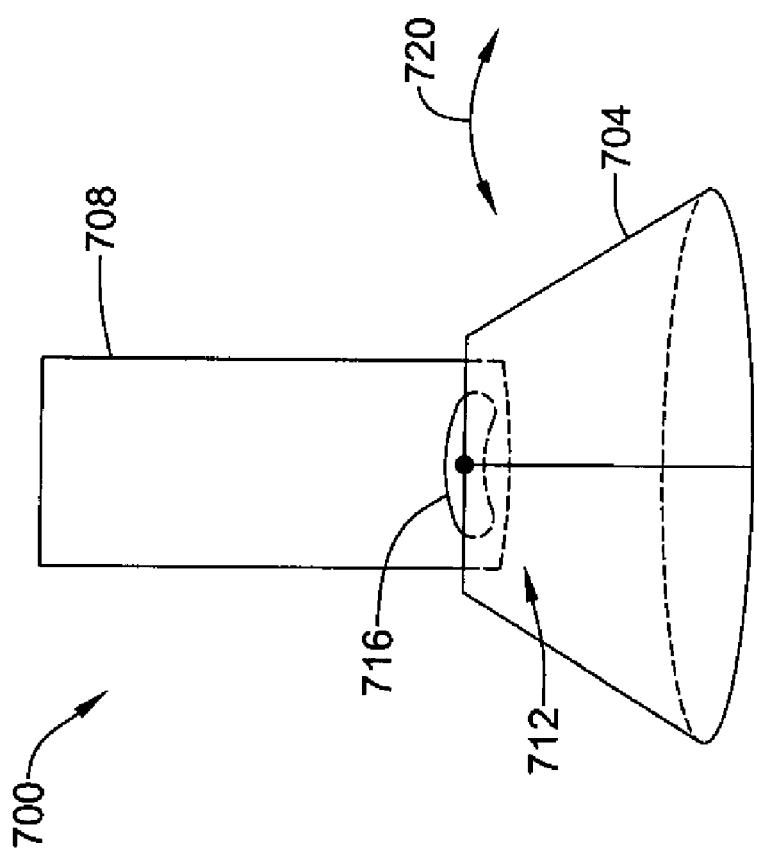
FIG. 24 is a side view of another embodiment of an access device.

FIG. 24 is another embodiment of an access device 700 that has a distal portion 704 and a proximal portion 708 that are coupled in a manner that enhances access to and visualization of a workspace exposed by the device. The device 700 is similar to those discussed above, except as set forth below. In some embodiments, the access device 700 includes a non-linear slot that enable movement of the access device 700 to facilitate access to and procedures at or near peripheral regions of the workspace that are not along a single axis. For example, in one embodiment, a junction 712 is provided that enables movement, e.g., tilting, of the proximal end to increase access to and visualization of peripheral regions, e.g., along a cephalad-caudal axis and along a medial-lateral axis. One embodiment that provides such movement includes an arcuate slot 716 that can be positioned on the proximal portion 708. The arrow 720 illustrates that the movement of the slot 716 relative to a fastener positioned therein is generally along an arc. Additionally, the movement of the proximal portion 708 relative to the distal portion 704 can be described as being cephalad-caudal and medial lateral.

The various devices, methods and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

Many of the devices, methods, techniques, and features described herein can be combined with many of the systems, apparatuses, methods and features disclosed in the patent applications of the Appendix. The entire disclosure of each of the following patent applications is placed in the Appendix, is hereby incorporated by reference herein, and is made a part of this specification: U.S. patent application Ser. No. 10/972,987 (filed Oct. 25, 2004), and PCT Patent Application, filed Sep. 30, 2004, entitled "METHODS, SYSTEMS AND APPARATUSES FOR PERFORMING MINIMALLY INVASIVE SPINAL PROCEDURES."

What is claimed is:

1. An access device for exposing an upper region of the spine of a patient, the device comprising:
a distal portion having an outer surface, an inner surface partially defining a passage extending along a longitudinal axis through the access device, the distal portion having a proximal end portion and a distal end portion, the distal end portion configured to conform to said upper region of said spine;
a proximal portion having an outer surface, an inner surface partially defining the passage, and at least one slot formed between the inner surface and the outer surface, the passage extending longitudinally from the proximal portion to the distal portion;
first and second fasteners coupling the distal portion with the proximal portion at first and second pivot points such that the distal and proximal portions pivot relative to each other along a first axis, wherein one fastener is coupled with the proximal end portion of the distal portion and configured to slide along the at least one slot to provide tilting of the proximal portion relative to the distal portion along a second axis, wherein the first axis is perpendicular to the second axis; and
a structure configured to reduce the stiffness of the distal portion to enhance tilting of the proximal portion relative to the distal portion, wherein the stiffness reducing structure comprises a cutout region located between the slot and at least one of a cephalad end and a caudal end of the device.

* * * * *